US010959975B1

(12) United States Patent
Cioe et al.

(10) Patent No.: US 10,959,975 B1
(45) Date of Patent: Mar. 30, 2021

(54) ANTIFUNGAL COMPOSITION, METHOD OF MAKING COMPOSITION, AND METHOD OF USING COMPOSITION

(71) Applicants: George A. Cioe, Narragansett, RI (US); The Tetra Corporation, Eaton Rapids, MI (US)

(72) Inventors: George A. Cioe, Narragansett, RI (US); Matthew W. Zoeller, Chicago, IL (US)

(73) Assignees: THE TETRA CORPORATION, Eaton Rapids, MI (US); George A. Cioe, Narragansett, RI (US)

( * ) Notice: Subject to any disclaimer, the term of this patent is extended or adjusted under 35 U.S.C. 154(b) by 0 days.

(21) Appl. No.: 16/023,824

(22) Filed: Jun. 29, 2018

Related U.S. Application Data

(60) Provisional application No. 62/618,289, filed on Jan. 17, 2018, provisional application No. 62/580,689, filed on Nov. 2, 2017.

(51) Int. Cl.
| | | |
|---|---|---|
| *A61K 9/00* | (2006.01) | |
| *A61K 8/34* | (2006.01) | |
| *A61K 8/04* | (2006.01) | |
| *A61K 8/06* | (2006.01) | |
| *A61K 9/08* | (2006.01) | |
| *A61K 47/44* | (2017.01) | |
| *A61Q 19/00* | (2006.01) | |
| *A61P 17/00* | (2006.01) | |
| *A61K 31/27* | (2006.01) | |
| *A61K 9/107* | (2006.01) | |
| *A61K 47/10* | (2017.01) | |
| *A61K 47/14* | (2017.01) | |

(52) U.S. Cl.
CPC ............ *A61K 31/27* (2013.01); *A61K 9/1075* (2013.01); *A61K 47/10* (2013.01); *A61K 47/14* (2013.01); *A61K 47/44* (2013.01)

(58) Field of Classification Search
CPC .. A61K 2300/00; A61K 31/355; A61K 45/06; A61K 47/10; A61K 9/10; A61K 47/54; A61K 47/44; A61K 2800/412; A61K 8/06; A61K 9/0014; A61K 47/14; A61K 2800/49; A61K 2800/262; A61K 2800/52; A61K 9/08; A61K 8/342; A01N 65/28; A01N 49/00; A61P 17/00; A61P 31/00; A61Q 19/00
See application file for complete search history.

(56) References Cited

U.S. PATENT DOCUMENTS

| | | | |
|---|---|---|---|
| 4,810,498 A | 3/1989 | DiMeglio | |
| 5,976,555 A * | 11/1999 | Liu | ............ A61K 8/06 424/401 |
| 6,440,437 B1 * | 8/2002 | Krzysik | ............... A61K 8/0208 424/400 |
| 6,699,488 B2 | 3/2004 | Deckner et al. | |
| 10,335,442 B1 | 7/2019 | Forrester et al. | |
| 2003/0082214 A1 | 5/2003 | Williams et al. | |
| 2003/0235541 A1 * | 12/2003 | Maibach | .............. A61K 9/0014 424/61 |
| 2006/0165823 A1 | 7/2006 | Herrera | |
| 2006/0210505 A1 | 9/2006 | Clapp et al. | |
| 2007/0258918 A1 | 11/2007 | Modi | |
| 2007/0292355 A1 | 12/2007 | Tamarkin et al. | |
| 2008/0070875 A1 | 3/2008 | Majewski et al. | |
| 2009/0269380 A1 | 10/2009 | Baker et al. | |
| 2009/0269394 A1 | 10/2009 | Baker et al. | |
| 2009/0280069 A1 * | 11/2009 | Godowski | ............ A61K 9/0014 424/45 |
| 2009/0324727 A1 * | 12/2009 | Foguet Roca | ........... A61K 8/06 424/489 |
| 2011/0195103 A1 * | 8/2011 | Perez Areas | ............. A61K 8/73 424/401 |
| 2012/0064135 A1 | 3/2012 | Levin et al. | |
| 2012/0149783 A1 * | 6/2012 | Aust | ...................... A61K 8/064 514/777 |
| 2013/0005774 A1 * | 1/2013 | Loupenok | ............ A61K 9/0014 514/336 |

(Continued)

FOREIGN PATENT DOCUMENTS

CA 2670715 C * 11/2015 ............... A61K 8/06

OTHER PUBLICATIONS

HawkinsWatts. HLB Balance. Date Retrieved: Apr. 18, 2019. <https://www.hawkinswatts.com/wp-content/uploads/2016/01/Hawkins-Watts-HLB-Balance.pdf>. (Year: 2019).*
O'Brien et al., "The Effectiveness and Safety of Australian Tea Tree Oil", Aug. 2007, Rural Industries Research and Development Corporation,pp. 1-16.
Gupta, "Topical Treatment of Onychomycosis as a Realistic Option to Systemic Therapy", J. Am., Podiatr. Med. Assoc., Jan./Feb. 2014, pp. 115-117.
Ryder et al., "Ergosterol biosynthesis inhibition by the thiocarbamate antifungal agents tolnaftate and tolciclate", Antimicrob. Agents and Chemother., 1986, 29(5), pp. 858-860.
Elewski et al., "The Use of 40% Urea Cream in the Treatment of Moccasin Tinea Pedis",Therapeutics for the Clinician, Dec. 3, 2003, pp. 355-357.

(Continued)

*Primary Examiner* — Tracy Liu
(74) *Attorney, Agent, or Firm* — Fitch, Even, Tabin & Flannery, L.L.P.

(57) ABSTRACT

A composition includes a microemulsion. The microemulsion includes an aqueous phase, an oil phase, and a surface-active agent. The aqueous phase includes water and at least one polyol. The oil phase includes a therapeutically effective amount of tolnaftate and a carrier including Jojoba oil. The microemulsion includes a disperse phase having a particle size of 50 nm or less. A method for making a composition includes forming a first mixture by combining water and at least one polyol; forming a second mixture by combining Jojoba oil, a surface-active agent, and a therapeutically effective amount of tolnaftate; and combining and mixing the first mixture and the second mixture to form a microemulsion. A method of using a composition includes applying the composition to a site of treatment.

20 Claims, No Drawings

(56) References Cited

U.S. PATENT DOCUMENTS

| | | | |
|---|---|---|---|
| 2013/0058985 A1* | 3/2013 | Willems | A61K 9/0014 424/400 |
| 2015/0148421 A1* | 5/2015 | Winn | A61K 8/345 514/575 |
| 2015/0157996 A1* | 6/2015 | Dussaud | B01F 17/0071 424/401 |
| 2017/0112764 A1* | 4/2017 | Wu | A61K 8/60 |
| 2018/0049981 A1* | 2/2018 | Foreman | A61K 9/1075 |
| 2019/0201531 A1 | 7/2019 | Forrester et al. | |

OTHER PUBLICATIONS

Iwatani et al.,"Two Mechanisms of Butenafine Action in Candida albicans", Antimicrob. Agents and Chemother., Apr. 1993, vol. 37, No. 4, pp. 785-788.

Georgopapadakou et al., "Effects of Squalene Epoxidase Inhibitors on Candida albicans", Antimicrob. Agents and Chemother., Aug. 1992, vol. 36, No. 8, pp. 1779-1781.

Nakai et al.,"Effects of Topical N-Acetylcysteine on Skin Hydration/Transepidermal Water Loss in Healthy Volunteers and Atopic Dermatitis Patients", vol. 27, No. 4, 2015, pp. 450-451.

Baran, "Review of antifungal therapy, part II: Treatment rationale, including specific patient populations", J. Dermatol. Treatment, 2008, 19, pp. 168-175.

Drake et al., "Effect of onychomycosis on quality of life", J. of Am. Acad. of Derm., 1998, vol. 38, No. 5, pp. 702-704.

Elkeeb et al.,"Transungual drug delivery: Current status", Int'l. J. of Pharmaceutics, 384, 2010, pp. 1-8.

Murdan, "Enhancing the nail permeability of topically applied drugs", Expert Opin. Drug Deliv., 2008, pp. 1267-1282.

Pan et al., "Urea: a comprehensive review of the clinical literature", Dermatology Online Journal—UC Davis, 19 (11), 2013, pp. 1-16.

Yamarik et al., "Final Report of the Safety Assessment of Urea", Int'l. J. of Toxicology, 24(Suppl. 3), 2005, pp. 1-56.

Berker, "Fungal Nail Disease", N. Engl. J. Med., 2009, pp. 2108-2116.

Roberts et al., "Guidelines for treatment of onychomycosis", Brit. J. of Dermatol., 2003; 148, pp. 402-410.

Gunt, "Hydration Effect on Human Nail Permeability", Pharm. Sci., Jun. 5, 2006, pp. 1-167.

Aslam et al.,"Role of antibiofilm-antimicrobial agents in controlling device-related infections", Int. J. Artif. Organs, 2011, 34(9), pp. 752-758.

"Cosmetic Chemistry of Natural Jojoba", pp. 1-28.

Santini et al.,"Cream Formulation Impact on Topical Administration of Engineered Colloidal Nanoparticles", PLOS ONE, May 11, 2015, p. 1-14

Miron et al., "Influence of penetration enhancers and molecular weight in antifungals permeation through bovine hoof membranes and prediction of efficacy in human nails", Eur. J. Pharm. Sci., 2014, 51, pp. 20-25.

Murdan, "Drug delivery to the nail following topical application", Int'l. J. Pharm., 236 (2002), pp. 1-26.

Oguz et al.,"Topical N-Acetylcysteine Improves Wound Healing Comparable to Dexpanthenol: An Experimental Study", Int. Surg., 2015,100, pp. 656-661.

Hao et al., "Mechanistic Study of Electroosmotic Transport Across Hydrated Nail Plates: Effects of pH and Ionic Strength", J. Pharm. Sci., 2008, 97(12): 5186-5197, pp. 1-19.

Grether-Beck et al.,"Urea uptake enhances barrier function and antimicrobial defense in humans by regulating epidermal gene expression", J. Invest Dermatol., Jun. 2012 ; 132(6): 1561-1572, pp. 1-23.

Baswan et al.,"Size and Charge Dependence of Ion Transport in Human Nail Plate", J. Pharm. Sci., 2016, 105(3): 1201-1208, pp. 1-23.

Goyal et al.,"Nanoparticles and nanofibers for topical drug delivery", J. Control Release, 2016, 240: 77-92, pp. 1-40.

Warshaw et al.,"NailQoL: a quality-of-life instrument for onychomycosis", Int'l. J. Dermatol., 2007, 46, pp. 1279-1286.

Szepietowski et al., "Factors Influencing Coexistence of Toenail Onychomycosis With Tinea Pedis and Other Dermatomycoses", Am. Dermatol., vol. 141, 2006, pp. 1-6.

Piérard, "Onychomycosis and Other Superficial Fungal Infections of the Foot in the Elderly: A Pan-European Survey", Dermatol., 2001, 202, pp. 220-224.

Abousamra et al.,"Solid Lipid Nanoparticles and Nanostructured Lipid Carriers of Tolnaftate: Design, Optimization and in-Vitro Evaluation", Int'l J. Pharmacy and Pharmaceutical Sci.,.vol. 8, Issue 1, 2016, pp. 380-385.

Moser et al., "Supersaturation: Enhancement of Skin Penetration and Permeation of a Lipophilic Drug", Pharm. Resch., vol. 18, No. 7, 2001, p. 1006.

Syed et al., "Treatment of toenail onychomycosis with 2% butenafine and 5% Melaleuca alternifolia (tea tree) oil in cream", Trop. Med. and Int'l. Health, 1999, vol. 4, No. 4, pp. 284-287.

Carson et al.,"Melaleuca alternifolia (Tea Tree) Oil: a Review of Antimicrobial and Other Medicinal Properties", Clin. Microb. Rev., 2006, vol. 19, No. 1, pp. 50-62.

May et al.,"Time-Kill studies of tea tree oils on clinical isolates", J. Antimicrob. and Chemother., (2000) 45, pp. 639-643.

Kobayashi et al.,"Enhancing effect of N-acetyl-L-cysteine or 2-Mercaptoethanol on the in Vitro Permeation of 5-Fluorouracil or Tolnaftate through the Human Nail Plate", Chem. Pharm. Bull., 1998, pp. 1797-1802.

Rajendra et al., "Transungual Drug Delivery: An Overview", J. Appl. Pharm. Sci. 02 (01), 2012: 203-209.

Brown, "A Basic Guide: Ungual Drug Delivery", pp. 10-11.

Vejnovic et al.,"Investigation of different formulations for drug delivery through the nail plate", Intl. J. Pharm., 386, 2010, p. 185-194.

Yale's Podiatric Medicine, p. 188.

AbouSamra et al., "Enhancement of the topical tolnaftate delivery for the treatment of tinea pedis via provesicular gel systems", J. of Liposome Res., 27(4), pp. 324-334.

May et al., Time-kill studies of tea tree oils on clinical isolates, J. Antimicrobial Chemotherapy, 2000, 45, pp. 639-643.

Carson et al., Melaleuca alternifolia (Tea Tree) Oil: a Review of Antimicrobial and Other Medicinal Properties, Clinical Microbiology Reviews, Jan. 2006, vol. 19, No. 1, pp. 50-62.

Flores et al., Antifungal Activity of Nanocapsule Suspensions Containing Tea Tree Oil on the Growth of Trichophyton rubrum, Mycopathologia, 2013, 175:281-286.

Maibach, Historical Perspectives and Clinical Efficacy, downloaded Aug. 9, 2010.

Washenik et al., Bioavailability and Efficacy: Corticosteriod Delivery in Foam Vehicle, downloaded Aug. 9, 2010.

Franz, Bioavailability and Topical Drugs, downloaded Aug. 9, 2010.

Feldman, Vehicles and Quality-of-Life Issues, downloaded Aug. 9, 2010.

de Souza et al., Antimicrobial activity of Melaleuca alternifolia nanoparticles in polymicrobial biofilm in situ, Microbial Pathogenesis, 113, 2017, 432-437.

\* cited by examiner

ANTIFUNGAL COMPOSITION, METHOD OF MAKING COMPOSITION, AND METHOD OF USING COMPOSITION

CROSS-REFERENCE TO RELATED APPLICATIONS

This non-provisional application claims priority of U.S. provisional application No. 62/580,689 filed on Nov. 2, 2017, and U.S. provisional application No. 62/618,289 filed on Jan. 17, 2018, the entire content of each of which is incorporated herein by reference.

FIELD

The present disclosure generally relates to compositions for treatment of fungal infections, methods for making such compositions, and methods of using such compositions.

BACKGROUND

Tolnaftate is an antifungal compound that is effective against an array of organisms including *Microsporum gypseum, M. canis, M. audouinii, M. japonicum, Trichophyton Rubrum, T. mentagrophytes, T. schoenleinni, T. tonsurans, Epidermophyton floccosum, Candida albacans,* and *Malassezia furfur*. Tolnaftate is the only monographed antifungal indicated for prophylaxis. Tolnaftate is well tolerated with a very minor adverse effect, i.e., a hypersensitivity to tolnaftate could cause pruritus and contact dermatitis. Resistance to tolnaftate has been reported only rarely. However, the potential to develop resistance by the action of multidrug efflux transporters does exist.

Tolnaftate is soluble in some solvents and chemicals. Many solvents are either not appropriate or do not serve as an effective vehicle for tolnaftate in medicines. For instance, a composition including formaldehyde as a tolnaftate vehicle was often prescribed for antipruritic and antifungal therapy. Dermatologists often used this medication as a treatment for pruritus because it gave the patient quick relief. Subsequently, the product was removed from the market when formaldehyde was identified as a carcinogen. As a result, many of the products available today are suspensions of tolnaftate.

Jojoba oil is extracted from the seed of the *Simmondsia chinensis* (Jojoba) plant. Jojoba oil is a natural source of liquid wax esters, like sperm whale oil. Jojoba oil contains an array of monounsaturated liquid wax esters including long chains of fatty acids and alcohols, whereas all other known seed oils are branched triglycerides. Jojoba oil has been widely used in cosmetics since the ban on the use of sperm whale oil in 1978.

Jojoba oil is lipophilic and chemically similar to the sebum produced by human sebaceous glands. As humans age, the production of sebum decreases and skin can dry and crack. Jojoba oil is capable of reconditioning skin for a natural luster and shine. Jojoba oil is also capable of dissolving excess sebum and allowing pores to transpire normally in younger humans.

The safety of natural Jojoba oil is well established. Jojoba oil is generally considered to not be allergenic, comedogenic, or an irritant to the eyes or skin. Jojoba is also generally considered not to promote contact sensitization. It has been found that bacteria including *Staphylococcus aureus* and *Pseudomonas* as well as the yeast *Candida albicans* are not capable of growing in Jojoba oil. Jojoba oil is generally understood to have a wide use and long history of not producing adverse effects.

The unique properties of Jojoba oil are suited to hold tolnaftate in solution. U.S. Pat. No. 4,810,498 to Paul J. DiMeglio, issued on Mar. 7, 1989, relates to a nail oil composition containing Jojoba oil and tolnaftate. See also U.S. RE36,253 reissued on Jul. 13, 1999. When applied to the body, Jojoba oil is miscible with sebum which makes Jojoba oil an effective vehicle for transporting tolnaftate to sequestered pathogens in pores and hair follicles. The properties of Jojoba oil made it the perfect vehicle for Tetra Corporation's Formula 3® antifungal. Formula 3® is a mixture of 5 oils. One of the oils, Jojoba oil, is the vehicle that holds tolnaftate in solution. Jojoba oil's moisture control and emollient qualities helped meet a requirement for simpler ingredients by replacing combinations of mineral oil, triglycerides, lanolin, squalene and synthetic esters. Jojoba oil's oxidative stability, thermal stability and lack of support for microbial growth allowed a decrease in dependence on antioxidants, preservatives, stabilizers and special handling requirements for tolnaftate in Formula 3®.

SUMMARY

A composition can generally include a microemulsion comprising an aqueous phase, an oil phase, and a surface-active agent. An aqueous phase can generally comprise water and at least one polyol. An oil phase can comprise a therapeutically effective amount of tolnaftate and a carrier comprising Jojoba oil. The microemulsion can be stabilized by the surface-active agent and generally comprise a disperse phase having a particle size of 50 nm or less. A method for making a composition can generally comprise forming a first mixture by combining water and at least one polyol; forming a second mixture by combining Jojoba oil, a surface-active agent, and a therapeutically effective amount of tolnaftate; and combining and mixing the first mixture and the second mixture to form a microemulsion. A method of using a composition can generally comprise applying the composition to a site of treatment.

DETAILED DESCRIPTION

Compositions according to the present disclosure generally include tolnaftate as an active pharmaceutical ingredient (API) in a microemulsion. Tolnaftate is FDA approved and an effective antifungal agent. The compositions are generally acceptable for use on humans and animals for the treatment of skin, hide, nails, hair, claws, hoofs, etc. The compositions include compounds that are active against fungi and components that allow the active compounds to reach the particular part of skin, nail, etc. that is infected by fungus. The compositions are generally non-systemic and can be applied topically to quickly flux through skin, a nail, etc. to treat ailments such as pruritus and fungal infections. The compositions facilitate delivery of a lipid soluble fraction comprising dissolved tolnaftate in an appropriate, dermatologically safe solvent mixture onto the skin, etc. The compositions can reduce the time required to relieve itching, scaling, cracking, burning, and irritation of skin, etc., by quickly delivering tolnaftate to the site of involvement. The compositions can also shorten the required duration of treatment, cosmetically condition skin and maintain skin's barrier function and healthy appearance. The compositions can be generally free-flowing to enable wicking action and quick absorption. The compositions can also be free of paraben, dye, and fragrance.

Tolnaftate is included in the compositions in part because the compound is generally recognized as a well-tolerated antifungal drug with few adverse effects. Tolnaftate is considered an API because the compound is an antifungal agent. Tolnaftate is an inhibitor of fungal squalene epoxidase and is considered noncompetitive and reversible. Epoxidase is membrane-bound and is part of the biosynthesis from acetate to sterols. Blocking epoxidase can result in the accumulation of squalene and deficiency in ergosterol. Ergosterol is considered the main sterol in fungi cell walls. Tolnaftate can attenuate mycelia growth and distort hyphae in fungi. Tolnaftate can be fungicidal or fungistatic depending on a concentration of the compound at a site of infection and the specific susceptibility of a target organism. In some aspects, compositions comprise tolnaftate in therapeutically effective amounts, such as amounts ranging from 0.1 to 2.0 w/w %, 0.3 to 1.7 w/w %, 0.5 to 1.5 w/w %, 0.90 to 1.10% w/w %, etc. Tolnaftate has been FDA approved in an amount of 1.0 w/w % and the FDA allows tolnaftate to be present in medicines in amounts from 0.9 to 1.15 w/w %. Tolnaftate has been found effective for treatment and prophylaxis of *Tinea pedis* (athlete's foot), *Tinea cruris* (jock itch), *Tinea corporis* (ringworm), as well as fungal infections nails, skin, etc.

However, the large branched shape of the tolnaftate molecule can hinder the flux of the molecule through skin, a nail, etc. The dimensions of energy minimized-structure of a tolnaftate molecule are measured to be 13.3×4.7×2.1 Å (1.33×0.47×0.21 nM). Therefore, compositions include tolnaftate in a carrier, e.g. one or more solvents, to facilitate transport through skin, etc. The tolnaftate molecule is sparsely soluble in water, but has much greater solubility in organic solvents, e.g., acetone, methylisobutyl ketone, chloroform, tetrahydrofuran, etc. However, due to the therapeutic application of the composition, tolnaftate is generally dissolved in a carrier that is safe and acceptable for formulation in any one or more of medicinal, cosmetic, health, beauty, veterinary products. The carrier should be acceptable for direct application onto skin, a nail, etc. In some aspects, the carrier has a relatively non-polar dipole moment and is capable of maintaining tolnaftate in solution when used in sufficient quantity and at typical product use temperatures of 12° C. (55° F.) and above.

In some embodiments, a carrier comprises Jojoba oil and any other solvent component useful for carrying tolnaftate. Jojoba oil has a character of comprising relatively linear mixed oleic mono esters, whereas most botanical oils have the character of the more polar triglyceride ester composition. Jojoba oil is keratinophilic, lipophilic and chemically similar to the sebum produced by human sebaceous glands. This allows a composition containing Jojoba oil to follow lipid pathways through stratum corneum and deliver a therapeutically effective amount of tolnaftate to a site of involvement. In addition, Jojoba oil includes straight chain double bonded molecules having thin dimensions, which aids Jojoba oil's penetration of keratin in skin, nails etc. The dimensions of energy-minimized structure of a Jojoba oil molecule are measured to be 35.0×12.1×2.6 Å (3.50×1.21×0.26 nM). The size of the Jojoba oil molecule also makes it possible for the oil to flux though keratin membranes with little or no lipophilic pathways.

With growing evidence and concern relating to the harm caused by oxygen free radicals, it is desirable for a carrier to have oxidative stability. Esters present in Jojoba oil have a high degree of oxidative stability and provide non-occlusive moisture control. Jojoba oil contains these unique esters and three types of tocopherols, which give the oil extraordinary oxidative and thermal stability. Jojoba's flammability at 640° F. is superior to the flammability of silicone at 400°–500° F. In addition, the nonvolatile nature of Jojoba oil can reduce Volatile Organic Compounds (VOC's) produced by a composition containing the oil. Jojoba oil can also be stored for long periods of time without concern for the oil becoming rancid or being depleted in antioxidants. The oxidative stability of Jojoba oil can also add shelf life to compositions in which the oil is added. Thus, the addition of Jojoba oil to a composition can reduce the necessity of adding antioxidants, preservatives, stabilizers, etc. to compositions. These properties make Jojoba a safe and effective carrier for antifungal compositions.

Jojoba oil also contains nutrients such as vitamin E, B complex vitamins, silicon, chromium, copper, and zinc. Without intending to be bound to any particular theory, it is also thought that iodine present in Jojoba oil may aid in fighting bacterial and fungal infections. Jojoba can also be used to treat acne, canker sores, cold sores, athlete's foot, warts, etc. The Jojoba oil included in compositions is preferably natural and not chemically altered or modified after extraction from the Jojoba plant. Jojoba seed wax, Jojoba butter, hydrogenated Jojoba oil, Jojoba esters, hydrolyzed Jojoba esters, isomerized Jojoba oil, Jojoba alcohol, synthetic Jojoba oil, etc. can be included in compositions, either in combination with or as a substitute for Jojoba oil. In some aspects, a composition can include Jojoba oil in any amount, such as amounts ranging from 1.0 to 45.0% w/w, 3.0 to 15.0 w/w %, 5.0 to 20.0 w/w %, 10.0 to 15.0 w/w %, etc.

In addition to Jojoba oil, a carrier can comprise solvents such as alkyl, oleic, and alkyl substituted aromatic esters. Solvents can also include alkyl esters of benzoic acid, naphthalenic acid, phthalic acid and similar alkyl esters of the homolog series C8 to C22 fatty acids and alcohols. The alkyl substituted ester C12-15 Alkyl Benozate is one such moiety. C12-15 Alkyl Benozate comprises a mixture of benzoic acid esters including benzoic acid and alcohols that have carbon chain lengths from 12 to 15. C12-15 Alkyl Benozate can serve as any one or more of a carrier, solvent, emollient, skin conditioning agent, etc. C12-15 Alkyl Benozate can provide a light conditioning and silky after touch to the skin folds around the nail & debrided nail. Solvents can also include any one or more of C16-17 Alkyl Benzoate, Stearyl Benzoate, Isostearyl Benzoate, Ethylhexyl Benzoate, and Octyldodecyl Benzoate. Solvents can also be derived from lower carbon chain linear alkyl esters such as amyl laurate. These may include moieties from the homolog monoester series C4 up to C22 alkyl chains. These esters may also be derived from homologs in the mono-unsaturated and poly-unsaturated oleic acid and alcohol series of similar carbon chain length, C8-C22. Other materials suitable for inclusion in carriers include mineral oil, triglycerides, lanolin, squalene and synthetic esters. In some aspects, a composition can include a solvent other than Jojoba oil in any amount, such as amounts ranging from 2.0 to 40.0% w/w, 5.0 to 20.0 w/w %, 10.0 to 30.0 w/w %, 15.0 to 25.0 w/w %, etc.

A composition can also include tocopherol, esters of tocopherol such as tocopherol acetate (Vitamin E Acetate) (commercial name: Coviox T-50), acetic acid ester of tocopherol, tocopheryl linoleate, tocopheryl linoleate/oleate, a mixture of linoleic and oleic acid esters of tocopherol, tocopheryl nicotinate, tocopheryl succinate, potassium ascorbyl tocopheryl phosphate, a salt of both vitamin E (Tocopherol) and vitamin C (Ascorbic Acid), dioleyl tocopheryl methylsilanol, tocophersolan (Tocopheryl Polyethylene Glycol 1000 Succinate), etc. Vitamin E Acetate can be included in a composition to serve as a moisturizer and a natural antioxidant favored for formula preservation via oxidation. Vitamin E acetate is a powerful antioxidant, possessing the ability to increase the moisturization of skin's horny layer and thereby improve surface relief. The dimensions of Jojoba oil can aid in penetrating a nail plate surface, opening layers of the nail, and drawing in Vitamin E Acetate. The antioxidant nature of Vitamin E Acetate can also serve to increase a shelf life of a composition.

Compositions can generally comprise a microemulsion (or nanoemulsion) having entropically stable rheology, meaning that the compositions do not separate or come apart. In some aspects, the compositions can comprise a microemulsion as defined by IUPAC. The physical state of the microemulsion provide the compositions with a translucent or clear appearance, unlike the opaque appearance of standard oil-in-water emulsions. The microemulsion can have physiochemical properties that facilitate the flux of tolnaftate to a site infected by an organism such as fungus, mold, yeast, etc. A microemulsion can generally include any structure such as a spherical micelle, cylindrical micelle, inverse spherical micelle, inverse cylindrical micelle, lamellar, bicontinuous, Windsor type I, II, III, IV, etc. A microemulsion can comprise a continuous phase and a disperse phase forming a dermatologically safe solvent mixture. In some aspects, a microemulsion can comprise droplet type dispersions either of oil-in-water (o/w) or of water-in-oil (w/o), with a size range in the order of less than 50 nm in drop radius. In some aspects, a dispersed phase can have a particle size, e.g. micelle size, of less than 50 nm, less than 25 nm, less than 10 nm, less than 5 nm, less than 1 nm, etc. A carrier can form either a continuous or a disperse phase including tolnaftate. A composition generally includes one or more surfactants to maintain a structured microemulsion.

In some embodiments, microemulsions are characterized as Windsor Type I oil-in-water microemulsions. These microemulsions generally include a continuous aqueous phase and a dispersed oil phase comprising a carrier and tolnaftate. Particles of a disperse phase can generally have a very small size, as described above, to effectuate transport of tolnaftate through layers of skin, a nail, etc. Generally, in some embodiments, a particle size of 10 nm can be sufficient to provide a composition capable of penetrating keratin.

An aqueous (water-based) phase can generally comprise water (aqua/eau) and any other component that is useful for the composition. Compositions can include water of any purity level. However, deionized water that is substantially free of minerals, salts, undesired chemicals, and other impurities is generally preferred. USP Purified Water is even more preferable. USP Purified Water is prepared from water complying with the regulations of the U.S. Environmental Protection Agency (EPA) with respect to drinking water. It contains no intentionally added substances. The quality of the water included in compositions can be monitored under and adhere to Good Manufacturing Practices outlined in the FDA's Guidance on Cosmetic Manufacturing Practice Guidelines, and in international guidelines on Good Manufacturing Practices known as ISO 22716. Water included in compositions can also be considered process water. Water can serve as a solvent in compositions and can form microemulsions with an oil-based phase. Water can also serve to hydrate the nail, skin, etc. In some aspects, a composition can include water in any amount, such as amounts ranging from 20 to 70% w/w, 25.0 to 65.0% w/w, 30.0 to 50.0% w/w, 30.0 to 60.0% w/w, 35.0 to 45.0% w/w, etc.

Polyols and alcohols can also be included in an aqueous phase to limit water activity and stabilize a microemulsion by acting as co-surfactants. Polyols and alcohols must also be acceptable for human and animal contact. An aqueous phase preferably includes one or more of a polyol and an alcohol, preferably two or more of a polyol and an alcohol, and even more preferably two or more polyols, to affect a stable microemulsion. Exemplary polyols include, but are not limited to, glycerin (glycerol), glycols, caprylyl glycol, propylene glycol, butylene glycol, hexylene glycol, pentylene glycol, 1,2-hexanediol, sorbitol, ethoxydiglycol, dipropylene glycol, etc. Butylene Glycol (1,3-Butanediol) is capable of dissolving essential oils and is a clear, nearly colorless, liquid. Caprylyl glycol can included in a composition as a preservative, an emollient, a solvent for aiding the dissolution of other components, as an antimicrobial agent, as an agent that increases the antimicrobial activity of preservatives, etc. Ethoxydiglycol can be included in a composition and serve as a penetration enhancer. Ethoxydiglycol can also potentiate n-acetyl cysteine in a composition. Compositions can also include phenoxyethanol as a preservative. In some aspects, a composition can include one or more of a polyol and an alcohol in any amount, such as amounts ranging from 3 to 50% w/w, 5 to 40% w/w, 10.0 to 35.0% w/w, 15.0 to 30.0% w/w, 20.0 to 25.0% w/w, etc.

Compositions can contain glycerin in any form, e.g., natural glycerin (plant or animal) or synthetic glycerin. While glycerin can serve as a stabilizing polyol in an aqueous phase of a composition, glycerin can also serve as a humectant, a viscosity decreasing agent, skin protectant, etc. Other humectants that can be included in compositions comprise aloe vera gel, alpha hydroxy acids, lactic acid, butylene glycol, glyceryl triacetate, hexylene glycol, maltitol, polymeric polyols, polyethylene glycol, polydextrose, propylene glycol, sorbitol, urea, xylitol, etc. In some aspects, a composition can include a humectant in any amount, such as amounts ranging from 1 to 50% w/w, 5 to 45% w/w, 7.0 to 40.0% w/w, 15.0 to 35.0% w/w, 20.0 to 25.0% w/w, etc.

An aqueous phase of a composition can also include water-soluble ingredients such as N-acetyl-1-cysteine (NAC) and urea. NAC can serve as a penetration enhancer and increase the flux of tolnaftate through keratin to the site of involvement. The effects of NAC are discussed in Kobayashi et al., "Enhancing Effect of N-Acetyl-L-cysteine or 2-Mercaptoethanol on the in Vitro Permeation of 5-Fluorouracil or Tolnaftate through the Human Nail Plate", *Chemical and Pharmaceutical Bulletin*, Volume 46 (1998) Issue 11 Pages 1797-1802; and Aslam et al., "Role of Antibiofilm-Antimicrobial Agents in Control of Device-Related Infections", *Int Artif Organs.*, 2011; 34(9): 752-758, the entire content of each of which is incorporated herein by reference. NAC can have bactericidal properties and break down bacterial biofilms of clinically relevant pathogens, e.g. *Pseudomonas aeruginosa, Staphylococcus aureus, Enterococcus faecalis, Enterobacter cloacae, Staphylococcus epidermidis*, and *Klebsiella pneumoniae*. NAC can also provide antioxidant effects. NAC can be used as a mucolytic agent for reduction of the viscosity of mucus and its removal. NAC can also serve as a skin conditioning agent and prevent oxidative stress and UV induced photoaging of skin.

Urea can provide any number of beneficial effects to a composition. Urea can provide hydrating effects since urea is strongly hygroscopic and draws and retains water within skin cells. Thus, urea can serve as a moisturizer and increase the water content of the top layers of the skin and dissolve the intercellular matrix, which results in loosening the horny layer of skin and shedding of scaly skin at regular intervals, thereby softening hyperkeratotic areas for cosmetic debridement and tolnaftate penetration. These effects will allow the oil phase, with tolnaftate, to penetrate more effectively. Urea can also provide penetration-assisting effects since urea can increase the penetration of other substances, e.g. corticosteroids, etc. as it increases skin hydration. Urea can provide keratolytic effects since urea is a debriding agent and softens the horny layer so it can be easily released from the surface of the skin. Urea can aid in regenerative skin protection since urea has a direct protective effect against drying influences. If used regularly, urea can improve the capacity of the epidermal barriers for regeneration. Urea can also provide irritation-soothing effects since urea has anti-pruritic activity based on local anesthetic effects. Urea can also minimize the change in the acid/base balance of a composition when other ingredients are added to the composition. Urea can also slow the loss of moisture from a product during use.

In some aspects, a composition can contain a mixture of ethylhexyl glycerin, caprylyl glycol, phenoxyethanol, which is commercially named Lincoserve HpH-4. This mixture can serve as a drop-in preservative for bacterial control and shelf-life stability.

Phospholipon 80 H and Lipoid S45 are examples of other tolnaftate penetration enhancers that can included in compositions and are discussed in AbuoSamra et al., "Enhancement of the topical tolnaftate delivery for the treatment of *Tinea pedis* via provesicular gel systems", *J Liposome Res.*, 2017 December, 27(4):324-334, the entire content of which is incorporated herein by reference.

A microemulsion can generally be stabilized by a surface-active agent. A surface-active agent can contain one or more, and preferably two or more surfactants. In some aspects, a composition can include a surface-active agent in any amount, such as amounts ranging from 7.0 to 70% w/w, 10.0 to 65.0% w/w, 10.0 to 30.0% w/w, 15.0 to 25.0% w/w, etc. In some aspects, the rheology of a microemulsion can be stabilized by preferably two or more amphiphilic surfactants that work together to create the desired properties. Surfactants can be generally based on organic compounds having a capacity to reduce surface tension at an oil/water interface. Generally, any number and combination of different types of surfactants can be combined and included in a composition to provide a microemulsion having desired structure and stability. In some embodiments, surfactants are selected from classes of nonionic and anionic ethoxylated compounds where the alkyl (lipid) moiety of the surfactant is given an enhanced hydrophilic character by an adduct of ethylene oxide polymerization. In some aspects, a suitable surface-active agent or surfactant can have an HLB (hydrophile-lipophile balance) value ranging from 3.0 to 14.0.

Useful surfactants also include a homolog series of mono-unsaturated oleyl alcohol ethers, e.g., Oleth-5. Oleth compounds are generally considered polyethylene glycol ethers of oleyl alcohol. Oleth compounds can range from liquids to waxy solids. The water solubility of Oleth compounds generally increases as the content of ethylene oxide in molecules of the compound increases. For example, Oleth-2, -3, -4, -5, -6, -7, -8, -9, -10, -11, -12, -15, -16, -20, -23, -25, -30, -40, -44, and -50 are polyethylene glycol ethers of oleyl alcohol in which the number in the name represents the average number of ethylene oxide units. Oleth ingredients are generally thought to reduce a surface tension of substances to be emulsified and help dissolution of ingredients in liquids in which the substances would not normally dissolve. Oleth ingredients can also help water mix with oil or dirt and thereby aid in the removal to remove these substances from skin, etc.

Other useful surfactants include ether adducts of dodecyl (C12), lauryl (C14), stearyl (C18) and other homologs of saturated fatty alcohols, e.g., Laureth-7. Surfactants can be derived from homologous alkyl and oleic esters, e.g., PEG-40 peroleate, PEG-25 hydrogenated castor oil. Surfactants can also include the alkyl homolog family of fatty alkanolamides, e.g., cocamide DEA, lauramide MEA. Additional useful surfactants include polysorbate 20, 21, 40, 60, 61, 65, 80, 81 and 85.

Surfactants can also be derived from ethoxylated adducts of lanolin, e.g., PEG-20 Hydrogenated Lanolin, PEG-25 hydrogenated lanolin. Polyethylene glycol (PEG) lanolin ingredients can be prepared from whole lanolin obtained from sheep sebaceous glands and sheered wool. Lanolin and hydrogenated lanolin can be reacted with ethylene oxide to form PEG lanolin and PEG hydrogenated lanolin. The numerical value in the PEG lanolin represents the average number of units of ethylene oxide added to each equivalent unit of lanolin to produce the corresponding PEG lanolin or PEG hydrogenated lanolin. PEG lanolin ingredients also help reduce a surface tension of substances to be emulsified and aid in the formation of microemulsions. PEG lanolin ingredients can also serve as skin lubricants and provide skin with a soft and smooth appearance.

Useful surfactants also include the alkyl and oleic homolog series of phosphate esters, which are anionic in character, e.g., Oleth-3 Phosphate, and dissociate to acid conditions when dispersed and hydrated in water. Oleth-3 Phosphate is commercially named Crodaofos O3A-LQ (the "A" standing for free acid and the "LQ" standing for liquid form). The lipophilic character of these phosphate esters can be modified in situ by addition of the appropriate organic alkali. This neutralizing agent may be from secondary and tertiary alkyl amines, e.g., diethanolamine, morpholine, and preferably aminomethyl propanol (commercially named: AMP-95). The neutralizing agent may also be derived from inorganic alkali, such as potassium hydroxide, sodium hydroxide or other hydroxides of alkaline earths. Aminomethyl propanol can also serve as a pH adjuster in a composition.

Compositions can also include Tea Tree Oil from the *Melaleuca alternifolia* (Tea Tree, Punktree, Paperbark-tree). Tea Tree Oil can be obtained by steam distillation of foliage of the Tea Tree. Tea Tree Oil is considered to include a combination of more than 100 components such as monoterpenes, sesquiterpenes, and terpene alcohols. Tea Tree Oil can of include 30-40% terpinen-4-ol, which provides antimicrobial and antifungal activity. Compositions can include Tea Tree Oil as an one or more of an anti-fungal, an antiseptic, an germicidal, an antibacterial, a preservative, a cleanser, etc.

A composition can also include one or more chelating agents, metal scavengers, etc. Exemplary compounds include ethylenediamine tetraacetic acid (EDTA) and its salts, Calcium Disodium EDTA, Diammonium EDTA, Dipotassium EDTA, Disodium EDTA, TEA-EDTA, Tetrasodium EDTA, Tripotassium EDTA and Trisodium EDTA, hydroxyethyl ethylenediamine triacetic acid (HEDTA), trisodium HEDTA, etc. Disodium EDTA and the related ingredients can bind and inactive to metal ions to prevent the degradation of a composition. Disodium EDTA can also maintain clarity, protect fragrance compounds, and prevent rancidity. EDTA, HEDTA and their salts can also serve as penetration enhancers.

Compositions can also include alkyl glyceryl ether ingredients, such as ethylhexylglycerin. Ethylhexylglycerin can serve as a microemulsion stabilizer in a composition by keeping a microemulsion from separating into oil and aqueous components. Ethylhexylglycerin can also enhance the function of preservatives in a composition by affecting cell walls of bacteria and promoting the destruction of the bacteria by the preservative. Ethylhexylglycerin can also serve to reduce odors and prevent formation of odors on skin, etc.

Jojoba oil, C12-15 Alkyl Benozate, glycerin, PEG-20 Hydrogenated Lanolin, Urea, Vitamin E Acetate, Caprylyl Glycol can also serve as cosmetic ingredients that restore the natural physical properties and appearance of skin.

A composition can include any electrolyte, e.g., sodium chloride, potassium chloride, magnesium sulfate, etc., suitable for reducing the viscosity of the composition.

In some aspects, a composition can include an any amount, such as 0.1 to 2.0 w/w %, 0.25 to 1.75, w/w %, 0.5 to 1.5 w/w %, etc.

Compositions can generally include any one or more of a suitable emollient, humectant, penetration enhancer, moisturizer, antioxidant, chelating agent, pH adjuster, stabilizer, preservative, metal scavenger, germicide, antibiotic, antimicrobial, antiseptic, antifungal, bactericide, vehicle, medication, antioxidant, penetration enhancer, carrier, solvent, surfactant, hydrating agent, soothing agent, numbing agent, cleanser, viscosity adjuster, etc.

While a component can be present in one phase of a microemulsion, the same component can also be present in one or more other phases, as permitted by solubility and transport of the component through various phases. Compositions including microemulsions carrying tolnaftate can be in the form of a gel, a paste, a liquid, etc.

In some embodiments, a microemulsion comprises about 1 w/w % tolnaftate, Jojoba oil, Oleth-3 phosphate, Oleth-5, Oleth-10, and butylene glycol, with the ratio of Oleth-3 phosphate to Oleth-5 to Oleth-10 to butylene glycol being 1:1.2:1.5:1.

In some embodiments, an antifungal microemulsion gel comprises tolnaftate USP 1.0 w/w %, Water (aqua), C12-15 Alkyl Benzoate, *Simmondsia Chinensis* (Jojoba) Oil, Glycerin, Oleth-10, Oleth-5, Oleth-3 Phosphate, PEG-20 Hydrogenated Lanolin, Butylene Glycol, Urea, Ethoxydiglycol, N-Acetyl-L-Cysteine, Tocopherol Acetate (Vitamin E), *Melaleuca alternifolia* (Tea Tree) Oil, Disodium EDTA, Ethylhexylglycerin, Caprylyl Glycol, Phenoxyethanol, Aminomethylpropanol, Sodium Chloride.

In some aspects, an oil-in-water microemulsion can comprise the following:

| | |
|---|---|
| Tolnaftate USP | 0.90-1.15 w/w % |
| Water (aqua) | 30.0-60.0 w/w % |
| C12-15 Alkyl Benzoate | 5.0-20.0 w/w % |
| Simmondsia Chinensis (Jojoba) Oil | 3.0-15.0 w/w % |
| Glycerin | 3.0-15.0 w/w % |
| Oleth-10 | 3.0-15.0 w/w % |
| Oleth-5 | 3.0-15.0 w/w % |
| Oleth-3 Phosphate | 3.0-15.0 w/w % |
| Butylene Glycol | 3.0-15.0 w/w % |
| PEG-20 Hydrogenated Lanolin | 3.0-15.0 w/w % |
| Urea | 1.0-10.0 w/w % |
| Ethoxydiglycol | 0.5-5.0 w/w % |
| N-Acetyl-L-Cysteine | 0.05-1.00 w/w % |
| Tocopherol Acetate (Vitamin E) | 0.01-0.30 w/w % |
| Melaleuca Alternifolia (Tea Tree) Oil | 0.01-0.10 w/w % |
| Disodium EDTA | 0.01-0.10 w/w % |
| Ethylhexylglycerin | 0.10-1.00 w/w % |

-continued

| | |
|---|---|
| Caprylyl Glycol | 0.10-1.00 w/w % |
| Phenoxyethanol | 0.10-2.00 w/w % |
| Aminomethylpropanol | 0.10-2.00 w/w % |

An antifungal composition can be made by generally any process that is useful for making microemulsions. Generally, an antifungal microemulsion can be made by a method including forming a first mixture by combining water and at least one polyol; forming a second mixture by combining Jojoba oil, a surface-active agent, and a therapeutically effective amount of tolnaftate; and combining and mixing the first mixture and the second mixture to form the microemulsion.

In some aspects of a method of making an antifungal microemulsion, deionized water can be combined with a chelating agent, a humectant, one or more polyols, a preservative, N-acetyl-1-cysteine, and urea to provide a first mixture. A second mixture can be prepared by combining a therapeutically effective amount of tolnaftate, Jojoba oil, Oleth-3 phosphate, and a co-surfactant. After separately and uniformly mixing the contents of the first and second mixtures, the first and second mixtures can be combined and mixed to form the microemulsion.

In some aspects, tolnaftate is dissolved in a combination of jojoba oil and C12-15 alkyl benzoate and emulsified at 80° C. to form a disperse phase in a continuous phase comprising mainly water and polyols. This microemulsion is of a Winsor Type I and comprises a lipid disperse phase emulsified within a continuous phase comprising a hydrophilic azeotrope of water/polyol or water/alcohol via use of an amphiphile, the latter being grouped surfactants in this case.

In some embodiments of a method of making an antifungal composition, a suitable amount of deionized water added to a first vessel and heated to about 80° C. Suitable amounts of a chelating agent, N-Acetyl-L-Cysteine, and sodium chloride are then added to the first vessel. Next, suitable amounts of a humectant, two or more polyols, a preservative, and urea are added to the water. In a second vessel, suitable amounts of C12-15 Alkyl Benzoate, Jojoba oil, and a surface-active agent are combined with a therapeutically effective amount of tolnaftate USP. The contents of the first and second vessels are then mixed under moderate conditions to provide a microemulsion composition.

A composition can generally have any properties suitable for the purpose of treatment, e.g. of an antifungal infection. In some aspects, a microemulsion can be a translucent viscous fluid at room temperature and may have a yellow color. In some aspects, a microemulsion can have a pH ranging from 4.0 to 6.0, and preferably from 4.50 to 5.50. In some aspects, a composition can have any viscosity, for example a viscosity at 25° C. ranging from 2,000 to 200,000, preferably 2,000 to 30,000 cps for a fluidic composition, preferably 10,000 to 30,000 cps for an intermediate viscosity, and preferably 30,000 to 200,000 cps for a sedentary gel. A composition can have any specific gravity (SpG), for example, a SpG at 25° C. ranging from 0.900 to 1.100, and preferably from 0.995 to 1.015. In some aspects, a composition can have a TPC of less than 100 cfu/g assessed using the USP<61> test method.

The compositions can be stored in any container, e.g., a jar, vial, a tube, a tube with integrated brush, packet, etc., that is suitable for dispensing by a physician, veterinarian, pharmacist, or over-the-counter sale. The compositions can be used for primary treatment of fungal infections or as a follow-up treatment where other compositions are ineffective. The compositions can be applied to a treatment site, e.g. skin, nail, etc., by a physician, a veterinarian, a patient, a caregiver, etc. A method of using a composition can comprise applying the composition to a site of treatment, such as by brushing, dropping, spreading, squirting, etc. the composition on the site.

Example

An oil-in-water microemulsion was made using the following process. A first stainless steel jacketed vessel (T5) equipped with an agitator and a side-sweep mixer was charged with 384.3 pounds (lb) of deionized water. The contents of the first vessel were then mixed at low speed and heated to 80° C. Next, 0.45 lb of Disodium EDTA, 2.25 lb of N-Acetyl-L-Cysteine, and 2.25 lb of Sodium Chloride were added to the first vessel under continued mixing until the added components dissolved. Under continued mixing at a low to moderate speed, the following components were added to the first vessel in the following order: 90.00 lb of Glycerine, 45.00 lb of Butylene Glycol, 4.50 lb of Ethoxydiglycol, 4.50 lb of Phenoxyethanol, and 6.30 of Lincoserve HpH-4. Next, 8.10 lb of AMP-95 Ultra 2000 was added to the first vessel while mixing. Next, with the contents of the first vessel held at 80° C., 9.00 lb of prilled urea was added under continued mixing. Mixing was then stopped, and the contents of the first vessel were held at 75-80° C. to produce Phase A.

A second jacketed stainless steel vessel (T8) was provided, and 108.00 lb of C12-15 Alkyl Benzoate and 54.00 lb of golden Jojoba oil were added to the second vessel and heated under slow mixing. Next, 9.45 lb of Tolnaftate USP was added to the contents of the second vessel under continued heating and mixing. Next, when the contents of the second vessel achieved a clear/uniform appearance at 60-70° C., the following components were added to the second vessel in the following order: 49.50 lb of Crodafos 03A-LQ, 45.00 lb of Oleth-5, and 76.50 lb of Oleth-10. Before proceeding, the contents of the second vessel were mixed until providing a uniform appearance. Next, with the contents of the second vessel held at 80° C., 0.45 lb of Coviox T-50 and 0.45 lb of Tea tree oil were added to the second vessel. The contents of the second vessel were then well-mixed to provide a uniform phase appearance at 80-85° C. Heating and mixing were then stopped to produce Phase B in the second vessel.

Next, the side sweep agitator was started in the first vessel and Phase B was transferred into Phase A at 12 rpm. The phases were mixed at 80 to 85° C. The contents of the first vessel were then well mixed for 10 minutes at 80° C. on moderate speed on a Lightnin mixer (200 rpm) and the agitator. Cooling of the first vessel was then initiated and the contents of the first vessel were mixed with side-sweep agitation only at 9 rpm. The Lightnin mixer was stopped to avoid aeration. The contents of the first vessel were then slowly cooled under slow mixing to avoid aeration. When the contents of the first vessel reached 45° C., the contents were recirculated for 10 minutes and then the mixing and cooling were stopped. The oil-in-water microemulsion in the first vessel was then tested for quality assurance and transferred through a 30 mesh 316S S gasket into steel drums for storage.

The oil-in-water microemulsion comprised:

| | |
|---|---|
| Deionized Water | 42.70 w/w % |
| Disodium EDTA | 0.05 w/w % |
| N-Acetyl-L-Cysteine | 0.25 w/w % |
| Sodium Chloride | 0.25 w/w % |
| Glycerine USP | 10.00 w/w % |
| Butylene Glycol | 5.00 w/w % |
| Ethoxydiglycol | 0.50 w/w % |
| Phenoxyethanol | 0.50 w/w % |
| Lincoserve HpH-4 | 0.70 w/w % |
| AMP-95 Ultra 2000 | 0.90 w/w % |
| Urea prilled | 1.00 w/w % |
| C12-15 Alkyl Benzoate | 12.00 w/w % |
| Jojoba Oil golden | 6.00 w/w % |
| Tolnaftate USP | 1.05 w/w % |
| Crodafos 03A-LQ | 5.50 w/w % |
| Oleth-5 | 5.00 w/w % |
| Oleth-10 | 8.50 w/w % |
| Coviox T-50 | 0.05 w/w % |
| Tea tree oil | 0.05 w/w % |

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:
1. An antifungal microemulsion comprising:
one or more of Oleth-5, Oleth-10, and Oleth-3 Phosphate,
an aqueous continuous phase comprising:
water;
one or more of butylene glycol, propylene glycol, glycerin, xylitol, ethylhexylglycerin, caprylyl glycol, sorbitol, phenoxyethanol, aminomethylpropanol, aminomethylpropanediol, and ethoxydiglycol;

N-acetyl-1-cysteine; and
urea;
a dispersed phase comprising:
a vehicle comprising *Simmondsia chinensis* Oil and C12-15 alkyl benzoate; and
tolnaftate dissolved in the vehicle, the antifungal microemulsion comprising 0.5 to 2.0 w/w % of tolnaftate.

2. The microemulsion of claim 1 comprising Oleth-5, Oleth-10, and Oleth-3 Phosphate.

3. The microemulsion of claim 1, the aqueous continuous phase comprising water, N-acetyl-1-cysteine, urea, butylene glycol, glycerin, ethylhexylglycerin, caprylyl glycol, phenoxyethanol, aminomethylpropanol, and ethoxydiglycol.

4. The microemulsion of claim 1 comprising Oleth-5, Oleth-10, and Oleth-3 Phosphate, and the aqueous continuous phase comprising water, N-acetyl-l-cysteine, urea, butylene glycol, glycerin, ethylhexylglycerin, caprylyl glycol, phenoxyethanol, aminomethylpropanol, and ethoxydiglycol.

5. The microemulsion of claim 1, further comprising PEG-20 Hydrogenated Lanolin.

6. The microemulsion of claim 1 further comprising one or more selected from a humectant, a moisturizer, antioxidant, a chelating agent, and a preservative.

7. The microemulsion of claim 1 further comprising one or more selected from tocopherol acetate, disodium EDTA, and *Melaleuca alternifolia* Oil.

8. The microemulsion of claim 1, the dispersed phase comprising a particle size of 50 nm or less.

9. An antifungal oil-in-water microemulsion comprising:
25.0 to 65.0 w/w % water;
0.5 to 2.0 w/w % tolnaftate;
5 to 40 w/w % of one or more of butylene glycol, propylene glycol, glycerin, xylitol, ethylhexylglycerin, caprylyl glycol, sorbitol, phenoxyethanol, aminomethylpropanol, aminomethylpropanediol, and ethoxydiglycol,
5.0 to 20.0 w/w % C12-15 Alkyl Benzoate;
0.05 to 1.00 w/w % N-acetyl-1-cysteine;
1.0 to 10.0 w/w % urea;
3.0 to 15.0 w/w % Jojoba oil; and
10.0 to 65.0 w/w % of one or more of Oleth-5, Oleth-10, and Oleth-3 Phosphate;
the microemulsion comprising an aqueous continuous phase and a dispersed phase, the aqueous continuous phase comprising water, urea, N-acetyl-l-cysteine, and the one or more of butylene glycol, propylene glycol, glycerin, xylitol, ethylhexylglycerin, caprylyl glycol, sorbitol, phenoxyethanol, aminomethylpropanol, aminomethylpropanediol, and ethoxydiglycol, the dispersed phase comprising Jojoba oil, tolnaftate, and C12-15 Alkyl Benzoate.

10. The microemulsion of claim 9 comprising 3.0 to 15.0 w/w % Oleth-10, 3.0 to 15.0 w/w % Oleth-5, and 3.0 to 15.0 w/w % Oleth-3 Phosphate.

11. The microemulsion of claim 9 comprising 3.0 to 15.0 w/w % glycerin, 3.0 to 15.0 w/w % butylene glycol, 0.5 to 5.0 w/w % ethoxydiglycol, 0.1 to 1.0 w/w % caprylyl glycol, 0.1 to 2.0 w/w % aminomethylpropanol 0.10 to 2.00 w/w % of phenoxyethanol, and 0.1 to 1.0 w/w % of ethylhexylglycerin.

12. The microemulsion of claim 9 further comprising one or more selected from a moisturizer, an antioxidant, a chelating agent, and a preservative.

13. The microemulsion of claim 11, further comprising one or more selected from 0.01 to 0.30 w/w % of tocopherol acetate, 0.01 to 0.10 w/w % of disodium EDTA, and 0.01 to 0.10 w/w % of *Melaleuca alternifolia* Oil.

14. The microemulsion of claim 9, the dispersed phase comprising a particle size of 50 nm or less.

15. A method of making an antifungal microemulsion, the method comprising:
forming a first mixture by combining water, urea, N-acetyl-1-cysteine, and one or more of butylene glycol, propylene glycol, glycerin, xylitol, ethylhexylglycerin, caprylyl glycol, sorbitol, phenoxyethanol, aminomethylpropanol, aminomethylpropanediol, and ethoxydiglycol;
forming a second mixture by combining Jojoba oil, C12-15 Alkyl Benzoate, tolnaftate, and one or more of Oleth-5, Oleth-10, and Oleth-3 Phosphate; and
combining and mixing the first mixture and the second mixture to form the antifungal microemulsion, a continuous phase of the antifungal microemulsion comprising the first mixture, and a dispersed phase of the antifungal microemulsion comprising the second mixture,
the antifungal microemulsion comprising 0.5 to 2.0 w/w % tolnaftate.

16. The method of claim 15, wherein the dispersed phase of the antifungal microemulsion comprises a particle size of 50 nm or less.

17. The microemulsion of claim 9 comprising 3.0 to 15.0 w/w % of Oleth-10, 3.0 to 15.0 w/w % of Oleth-5, and 3.0 to 15.0 w/w % of Oleth-3 Phosphate, 3.0 to 15.0 w/w % glycerin, 3.0 to 15.0 w/w % butylene glycol, 0.5 to 5.0 w/w % ethoxydiglycol, 0.1 to 1.0 w/w % caprylyl glycol, 0.1 to 2.0 w/w % aminomethylpropanol, 0.10 to 2.00 w/w % of phenoxyethanol, and 0.1 to 1.0 w/w % of ethylhexylglycerin.

18. The method of claim 15, wherein the first mixture comprises water, urea, N-acetyl-1-cysteine, butylene glycol, glycerin, ethylhexylglycerin, caprylyl glycol, phenoxyethanol, aminomethylpropanol, and ethoxydiglycol.

19. The method of claim 15, wherein the second mixture comprises Jojoba oil, C12-15 Alkyl Benzoate, tolnaftate, Oleth-5, Oleth-10, and Oleth-3 Phosphate.

20. The method of claim 15, wherein the first mixture comprises water, urea, N-acetyl-1-cysteine, butylene glycol, glycerin, ethylhexylglycerin, caprylyl glycol, phenoxyethanol, aminomethylpropanol, and ethoxydiglycol; and the second mixture comprises Jojoba oil, C12-15 Alkyl Benzoate, tolnaftate, Oleth-5, Oleth-10, and Oleth-3 Phosphate.

* * * * *